United States Patent
Lee

(10) Patent No.: US 9,141,761 B2
(45) Date of Patent: Sep. 22, 2015

(54) APPARATUS AND METHOD FOR ASSISTING USER TO MAINTAIN CORRECT POSTURE

(75) Inventor: Ho-Sub Lee, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 451 days.

(21) Appl. No.: 13/420,789

(22) Filed: Mar. 15, 2012

(65) Prior Publication Data

US 2013/0072820 A1 Mar. 21, 2013

(30) Foreign Application Priority Data

Sep. 20, 2011 (KR) ........................ 10-2011-0094854

(51) Int. Cl.
| G08B 23/00 | (2006.01) |
| G06F 19/00 | (2011.01) |
| A61B 5/107 | (2006.01) |

(52) U.S. Cl.
CPC .......... *G06F 19/3431* (2013.01); *A61B 5/1071* (2013.01)

(58) Field of Classification Search
CPC .. A61B 5/1116; A61B 5/1118; A61B 5/1128; A61B 5/4561; A61B 5/4566; A61B 5/4538; A61F 2/00
USPC .................. 600/549, 594, 587; 340/575, 576, 340/573.3; 345/169
See application file for complete search history.

(56) References Cited

U.S. PATENT DOCUMENTS

| 6,483,485 | B1 | 11/2002 | Huang et al. | |
| 7,778,444 | B2 | 8/2010 | Lee et al. | |
| 8,810,413 | B2 * | 8/2014 | Wong et al. | 340/575 |
| 2006/0129059 | A1 | 6/2006 | Kim et al. | |
| 2008/0068184 | A1 * | 3/2008 | Bonefas et al. | 340/575 |
| 2009/0324024 | A1 | 12/2009 | Worthington | |
| 2011/0080290 | A1 | 4/2011 | Baxi et al. | |
| 2011/0080345 | A1 * | 4/2011 | Jun et al. | 345/169 |

FOREIGN PATENT DOCUMENTS

| JP | 2011-90421 A | 5/2011 |
| KR | 10-2005-0084263 A | 8/2005 |
| KR | 10-2006-0124207 A | 12/2006 |
| KR | 10-0657917 B1 | 12/2006 |
| KR | 10-2007-0071308 A | 7/2007 |
| KR | 10-2008-0001768 A | 1/2008 |
| WO | WO 2011/046208 A1 | 4/2011 |

OTHER PUBLICATIONS

European Search Report issued Sep. 2, 2013 in counterpart European Patent Application No. 12184924.4 (8 pages In English).

(Continued)

*Primary Examiner* — Brian Szmal
(74) *Attorney, Agent, or Firm* — NSIP Law

(57) ABSTRACT

An apparatus for assisting a user to maintain a correct posture is provided. The apparatus includes a determining unit configured to determine whether the user is using a portable terminal in a correct posture based on a user's face image captured by the portable terminal, an angle of inclination of the portable terminal, or any combination thereof, and an alarming unit configured to provide a predetermined alarm according to a result of determination by the determining unit.

12 Claims, 10 Drawing Sheets

(56) References Cited

OTHER PUBLICATIONS

Jaimes, Alejandro, et al. "Sit straight (and tell me what I did today): a human posture alarm and activity summarization system." Proceedings of the 2nd ACM workshop on Continuous archival and retrieval of personal experiences. ACM, 2005.

Lee, Hosub, et al. "A new posture monitoring system for preventing physical illness of smartphone users." Consumer Communications and Networking Conference (CCNC), 2013 IEEE. IEEE, 2013.

* cited by examiner

APPARATUS AND METHOD FOR ASSISTING USER TO MAINTAIN CORRECT POSTURE

CROSS-REFERENCE TO RELATED APPLICATION(S)

This application claims the benefit under 35 U.S.C. §119 (a) of Korean Patent Application No. 10-2011-0094854, filed on Sep. 20, 2011, in the Korean Intellectual Property Office, the entire disclosure of which is incorporated herein by reference for all purposes.

BACKGROUND

1. Field

The following description relates to an apparatus and a method for assisting user to maintain correct posture.

2. Description of the Related Art

An increasing number of users are experiencing a variety of contents through a portable terminal including, for example, a smartphone, a tablet PC, or the like. The contents may include digital media broadcasting, games, movies etc. In particular, younger users may select to use their smartphone or a tablet PC while lowering their head and placing the portable terminal close to their waist or on their knees while traveling, for example, on the bus or subway. In response to a user using the portable terminal for a long period of time in such a posture, the user's cervical spine may be strained. A cervical spine normally has a C-shaped curve, and in response to a person viewing a screen while lowering or craning his or her neck for prolonged period, the user may be highly likely to have a forward head posture. Due to the prolonged period of having a forward head posture, the user may develop a straight cervical spine. A straightened cervical spine may reduce the ability of the neck to absorb an impact. Thus, an increase in the occurrence of a cervical disc may be likely.

According to a Korean spinal pain clinic report, in an analysis on the number of cervical disc patients in October 2009, when smartphones were first released in Korea, and April 2010, around which the smartphones were considered to be widely used, the analysis indicates that the number of cervical disc patients under thirty increased from 38 to 149, which is a 390 percent increase. In addition, the number of patients in the 41-49 age group, which was 69 in October 2009, increased to 129 in April 2010. On the other hand, there were only a 39 percent increase and 37 percent increase in the number of cervical disc patients in their 50s and 60s, respectively. In addition, a user of the smartphone may be subject to dry eyes (xerophthalmia). Dry eyes may be caused by watching a screen too closely. In response to a person having dry eyes, the person may feel their eyes burning, stinging or the like. Also, their eyes may tire very easily, making it difficult to keep their eyes open. A decrease in the secretion of tears is one common cause of dry eyes. People may forget to blink while watching TV, reading books or the like with concentration, and this lack of blinking may result in a reduction of tear secretion. Accordingly, a user of the smartphone having a smaller display than a TV may concentrate even more on the display of the smartphone at a closer range. Thus, a higher probability for the smartphone users to have dry eyes may exist.

To prevent a smartphone user from having a forward head posture and dry eyes, the smartphone user may need to reduce usage time of the smartphone, and, during use of the smartphone, keep the smartphone at eye level. In addition, in response to the user using the smartphone for more than ten minutes, the user may need to regularly stretch or intentionally blink their eyes frequently.

As another aspect, reducing the usage time of the smartphone/tablet PC in light of the advanced mobility and a variety of functions and contents served by the device may not be practical. Many users may not recognize such risks, and even when the users do the risks, many users may not pay enough attention to maintain a correct posture. Thus, a device to actively promote a user to take a correct posture or to alarm the user of the possible risk may be needed.

SUMMARY

According to an aspect, an apparatus for assisting a user to maintain a correct posture is provided. The apparatus includes a determining unit configured to determine whether the user is using a portable terminal in a correct posture based on a user's face image captured by the portable terminal, an angle of inclination of the portable terminal, or any combination thereof, and an alarming unit configured to provide a predetermined alarm according to a result of determination by the determining unit.

The determining unit may estimate a state of the user's cervical spine, a state of user's viewing the portable terminal as a criterion for determining the correct posture, or any combination thereof.

The determining unit may include a cervical state estimating unit configured to estimate a degree of tilt of the user's cervical spine as the state of the cervical spine based on the user's face image, the angle of inclination of the portable terminal, or any combination thereof.

The determining unit may include a viewing state estimating unit configured to estimate a distance between user's eyes and the portable terminal or a state of user's concentration on the portable terminal, as the state of the user's viewing the portable terminal, based on the user's face image.

In another aspect, an apparatus for assisting a user to maintain a correct posture is provided. The apparatus includes a sensor unit configured to collect a user's face image captured by a portable terminal and an angle of inclination of the portable terminal, a cervical spine state estimating unit configured to estimate a state of the user's cervical spine based on the user's face image, the angle of inclination of the portable terminal, or any combination thereof, and an alarming unit configured to provide a predetermined alarm according to a result of estimation of the cervical spine state estimating unit.

The cervical spine state estimating unit may determine whether the state of the user's cervical spine is in a normal range or falls outside a normal range based on a result of comparison between a previously stored reference face image and a currently capture face image.

The cervical spine state estimating unit may determine whether the state of the user's cervical spine is in a normal range or falls outside a normal range based on a result of comparison between a predefined threshold value and the angle of inclination of the portable terminal.

The cervical spine state estimating unit may preliminarily determine whether the state of the user's cervical spine is in a normal range or falls outside a normal range based on a result of comparison between a previously stored reference face image and a currently captured face image and finally determines whether the state of the user's cervical spine is in a normal range or falls outside a normal range based on a result of comparison between a predefined threshold value and the angle of inclination of the portable terminal.

The apparatus may include a pattern storage unit configured to receive the user's face image and the angle of inclination of the portable terminal from the sensor unit and to extract a feature point from the face image and store a result of matching between the extracted feature point and the angle of inclination of the portable terminal.

The apparatus may include a user setting unit configured to set a parameter for the cervical spine state estimating unit and a type of the alarm to be provided by the alarming unit in response to a user's input.

The predetermined alarm may include an alarm message on a display of the portable terminal, an alarming sound, a vibration, or a decrease in power sent to the display.

In another aspect, an apparatus for assisting a user to maintain a correct posture is provided. The apparatus includes a sensor unit configured to sense a user's face image captured by a portable terminal and an angle of inclination of the portable terminal, a cervical spine state estimating unit configured to estimate whether a state of the user's cervical spine state is in a normal range or falls outside a normal range based on the user's face image, the angle of inclination of the portable terminal, or any combination thereof, a viewing state estimating unit configured to estimate whether a state of the user's viewing the portable terminal is in a normal range or falls outside a normal range based on the user's face image in response to the cervical spine state estimating unit determining that the state of the user's cervical spine is in the normal range, and an alarming unit configured to provide a predetermined alarm in response to the state of the user's cervical spine or the state of the user's viewing the portable terminal falling outside the normal range.

The cervical spine state estimating unit may determine whether the state of the user's cervical spine is in the normal range or falls outside the normal range based on a result of comparison between a previously stored reference face image and a currently captured face image.

The cervical spine state estimating unit may determine whether the state of the user's cervical spine is in the normal range or falls outside the normal range based on a result of comparison between a predefined threshold value and the angle of inclination of the portable terminal.

The cervical spine state estimating unit may preliminarily determine whether the state of the user's cervical spine is in the normal range or falls outside the normal range based on a result of comparison between a previously stored reference face image and a currently captured face image and finally determine whether the state of the user's cervical spine is in the normal range or falls outside the normal range based on a result of comparison between a predefined threshold value and the angle of inclination of the portable terminal.

The viewing state estimating unit may calculate a distance between the user's eyes and the portable terminal based on a ratio of an area of a face region to the entire face image and determine whether the state of the user's viewing the portable terminal is in the normal range or falls outside the normal range according to the calculated distance.

The viewing state estimating unit may calculate a degree of the user's concentration on the portable terminal based on information about eye movement in the user's face image and determine whether the state of the user's viewing the portable terminal is in the normal range or falls outside the normal range according to the calculated degree of concentration.

The viewing state estimating unit may calculate a distance between the user's eyes and the portable terminal based on a ratio of an area of a face region to the entire face image, preliminarily determine whether the state of the user's viewing the portable terminal is in the normal range or falls outside the normal range according to the calculated distance, calculate a degree of the user's concentration on the portable terminal based on information about eye movement in the user's face image and finally determine whether the state of the user's viewing the portable terminal is in the normal range or falls outside the normal range according to the calculated degree of concentration.

The apparatus may further include a pattern storage unit configured to receive the user's face image and the angle of inclination of the portable terminal from the sensor unit and to extract a feature point from the face image and store a result of matching between the extracted feature point and the angle of inclination of the portable terminal.

The apparatus may further include a user setting unit configured to, in response to a user's input, set a parameter for the cervical spine state estimating unit, a parameter for the viewing state estimating unit and a type of an alarm to be provided by the alarming unit.

The state of the cervical spine may be the angle of the user's head with respect to the user's torso.

In another aspect, a method for assisting a user to maintain a correct posture is provided. The method includes determining whether a state of a user's cervical spine or a state of user's viewing a portable terminal is in a normal range or falls outside a normal range based on a user's face image captured by the portable terminal, an angle of inclination of the portable terminal, or any combination thereof, and providing a predetermined alarm in response to the state of the user's cervical spine or the state of the user's viewing the portable terminal falling outside the normal range.

The determining may include determining whether the state of the user's cervical spine is in a normal range or falls outside a normal range based on a result of comparison between a previously stored reference face image and a currently capture face image.

The determining may include whether the state of the user's cervical spine is in the normal range or falls outside the normal range based on a result of comparison between a predefined threshold value and the angle of inclination of the portable terminal.

The determining may include preliminarily determining whether the state of the user's cervical spine is in the normal range or falls outside the normal range based on a result of comparison between a previously stored reference face image and a currently captured face image and finally determining whether the state of the user's cervical spine is in the normal range or falls outside the normal range based on a result of comparison between a predefined threshold value and the angle of inclination of the portable terminal.

The determining may include calculating a distance between user's eyes and the portable terminal based on a ratio of an area of a face region to the entire face image and determining whether the state of the user's viewing the portable terminal is in the normal range or falls outside the normal range according to the calculated distance.

The determining may include calculating a degree of the user's concentration on the portable terminal based on information about eye movement in the user's face image and determining whether the state of the user's viewing the portable terminal is in the normal range or falls outside the normal range according to the calculated degree of concentration.

The determining may include calculating a distance between the user's eyes and the portable terminal based on a ratio of an area of a face region to the entire face image, preliminarily determining whether the state of the user's viewing the portable terminal is in the normal range or falls outside the normal range according to the calculated distance, calculating a degree of the user's concentration on the portable terminal based on information about eye movement in the user's face image and finally determining whether the state of the user's viewing the portable terminal is in the normal range or falls outside the normal range according to the calculated degree of concentration.

In another aspect, a device is provided. The device includes an apparatus for assisting a user to maintain a correct posture comprising an alarming unit configured to provide a predetermined alarm according to a result of determination based on a determination on whether a user is using a portable terminal in a correct posture based on the user's face image captured by a portable terminal, an angle of inclination of the portable terminal, or any combination thereof.

Other features and aspects may be apparent from the following detailed description, the drawings, and the claims.

Figure 1:
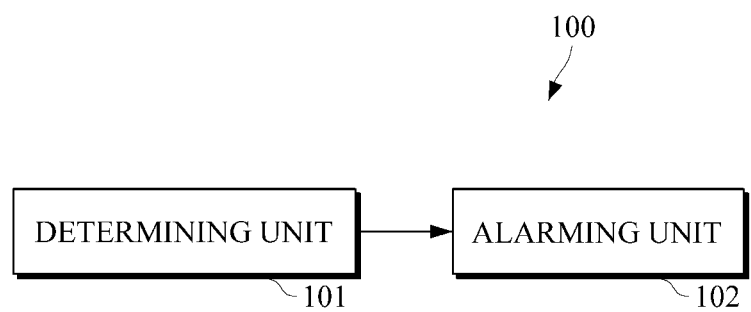
FIG. 1 is a diagram illustrating an example of an apparatus for assisting a user to maintain a correct posture during use of a portable terminal.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

FIG. 1 illustrates an example of an apparatus for assisting a user to maintain a correct posture during use of a portable terminal.

Referring to FIG. 1, apparatus 100 may be a portable terminal. The portable terminal may be a mobile phone, a smart-phone, an MP3 player, a portable multimedia player (PMP), a tablet and the like. The portable terminal may include a variety of sensors.

The apparatus 100 includes a determining unit 101 and an alarming unit 102. Each of the determining unit 101 and the alarming unit 102 may be implemented as either hardware to be installed inside the portable terminal or software to be executed by hardware equipped in the portable terminal. The hardware may include a processor. In addition, the determining unit 101 and the alarming unit 102 may be integrated as one unit, and a part of function to be executed by one functional unit may be performed by one or more other functional units. As another example, the determining unit 101 and the alarming unit 102 may be implemented as separate units.

The determining unit 101 may receive information on a user's face image of a user taken by the portable terminal, a tilt angle of the portable terminal, or any combination thereof. For example, the determining unit 101 may receive information on a user's face image from a front camera equipped in the portable terminal and may receive information on a tilt angle of the portable terminal. An orientation sensor, or combination of an accelerometer and a magnetic sensor located on the portable terminal may provide the tilt angle information.

The determining unit 101 may determine whether the user is using the portable terminal in a correct posture based on the received information on the user's face image, the tilt angle of the portable terminal, or any combination thereof. For example, the determining unit 101 may estimate the state of the user's cervical spine, the user's viewing of the portable terminal, or any combination thereof. The state of the cervical spine may indicate an angle of the user's head with respect to the user's torso. In other words, the state of the cervical spine may indicate the degree of the tilt of the neck. The state of the user's viewing of the portable terminal may indicate a distance between the user's eyes and the portable terminal or correspond to a degree of the user's concentration on the portable terminal.

In one example, the determining unit 101 may determine that the user is not in a correct posture in response to the state of the user's cervical spine not being in the predefined range of a correct posture. For example, in response to the user using the portable terminal for a significant amount of time with the user's neck tilted at an angleover a specific threshold tilt angle, the determining unit 101 may determine that the user is not in a correct posture.

In another example, the determining unit 101 may determine that the user is not in a correct posture in response to the state of the user's viewing of the portable terminal not being in a predefined normal range. For example, in response to the user viewing the portable terminal at a distance closer than a threshold distance or keeping an eye on a part of the portable terminal for a long period of time, the determining unit 101 may determine that the user is not in a correct posture.

In another example, the determining unit 101 may determine whether the user is in a correct posture based on both the state of the cervical spine and the state of the viewing of the portable terminal. For example, the determining unit 101 may determine that the user is not in a correct posture in response to either the state of the cervical spine or the state of the viewing of the portable terminal not being in a normal range, or the determining unit 101 may preliminarily estimate the state of the cervical spine. In response to the state of the cervical spine indicating a probability that the user is not in a correct posture, the determining unit 101 may estimate the state of the viewing of the portable terminal. In another example, the state of the viewing of the portable terminal may be preliminarily estimated and then in response to the result of the estimation showing that the user is not in a correct posture, the state of the cervical spine may be finally estimated.

The alarming unit 102 may provide a predefined alarm based on a determination of the determining unit 101 that the user is not in a correct posture. The alarm may not be limited by its type. For example, the alarming unit 102 may provide an alarm in the form of an image, text, sound, vibration, or the combination thereof. For example, the alarming unit 102 may display an alarm message on a display of the portable terminal, generate an alarming sound, a vibration, or decrease the power sent to the display. In addition, the alarming unit 102 may display a specific activity on the display of the portable terminal, for example, the specific activity may be a stretching exercise, or change the way a screen is displayed so as to induce the user to change their posture, for example, the screen may be displayed 3-dimensionally.

Figure 2:
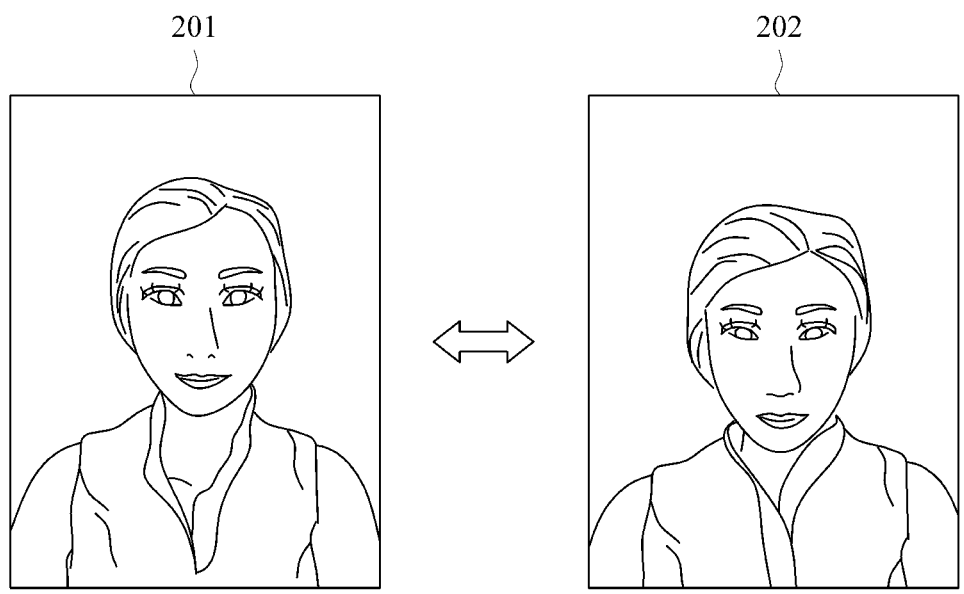
FIG. 2 is a diagram illustrating an example of a method of estimating a state of the cervical spine.

FIG. 2 illustrates an example of a method of estimating a state of the cervical spine.

Referring to FIGS. 1 and 2, the determining unit 101 may determine whether the state of the cervical spine falls within a normal range or falls outside the normal range based on a result of a comparison between a previously stored reference face image 201 and a currently captured face image 202.

In the example, the reference face image 201 may be a face image of a user taken in a correct posture. The determining unit 101 may determine whether the state of the cervical spine falls within a normal range or falls outside the normal range. The determination may occur based on a result of a comparison between features of the reference face image 201 and features of the captured face image 202. The features may include a shape of a face, a ratio of the area of the face and the area of a neck, and the brightness of a face. For example, the face image 202 captured in response to the user lowering his/her head may show a more oval-shaped face, less neck, or a less bright face in comparison to the reference face image 201. In response to features of the captured face image 202 not falling within a predefined threshold range, the determining unit 101 may determine that the state of the user's cervical spine falls outside the normal range. In other words, the determining unit 101 may determine that the captured face image 202 is not similar to the reference face image 201. In addition, in response to the state of the user's cervical spine falling outside a normal range, the determining unit 101 may determine that the user is using the portable terminal in an improper posture.

In another example, the reference face image 201 may include a plurality of images taken with respect to various tilt angles of the cervical spine. The determining unit 101 may extract the reference face image 201 having features most similar to features of the captured face image 202, and infer a current tilt angel of the user's cervical spine based on the extracted reference face image 201. In response to the inferred tilt angle of the cervical spine falling outside a predefined threshold range, the determining unit 101 may determine that the state of the user's cervical spine falls outside a normal range. In addition, in response to the state of the user's cervical spine falling outside the normal range, the determining unit 101 may determine that the user is using the portable terminal in an improper posture.

Figure 3:
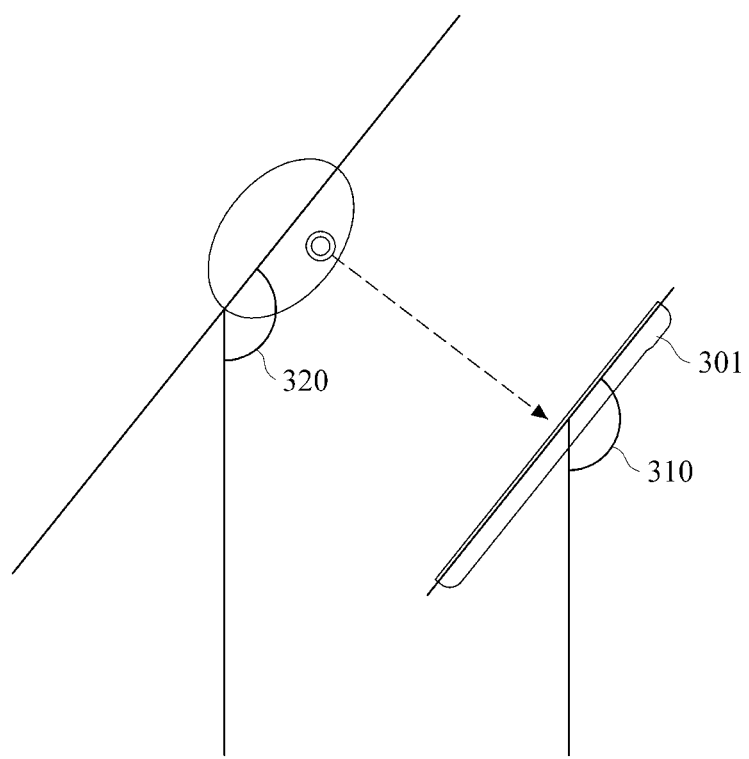
FIG. 3 is a diagram illustrating another example of a method of estimating a state of the cervical spine.

FIG. 3 illustrates another example of a method of estimating the state of the cervical spine.

Referring to FIGS. 1 and 3, in consideration of a viewing angle as a usage characteristic of a portable terminal, a degree of inclination of the portable terminal 301 may substantially correspond with a degree of tilt of the user's neck. Thus, the determining unit 101 may determine that the degree of inclination of the portable terminal 301 substantially corresponds with the degree of tilt of the user's cervical spine. For example, the determining unit 101 may collect sensor information from a variety of sensors, calculate an inclination angle 310 of the portable terminal 301 based on the collected sensor information, and calculate the tilt angle of the user's cervical spine based on the calculated inclination angle 310. The variety of sensors may include an orientation sensor, an acceleration sensor, a magnetic sensor, or the like, which is equipped in the portable terminal 301. In response to the tilt angle 320 of the user's cervical spine not falling within a predefined threshold range, the determining unit 101 may determine that the state of the user's cervical spine falls outside a normal range. In addition, in response to the user's cervical spine not falling within the normal range, the determining unit 101 may make a determination that the user is using the portable terminal 301 in an improper posture.

The examples shown in FIGS. 2 and 3 illustrate a method of estimating a state of the user's cervical spine based on a face image and based on a degree of inclination of the portable terminal. However, the examples are only for illustrative purposes and the method of estimation of a state of the user's cervical spine is not limited thereto. For example, the state of the user's cervical spine may be preliminarily estimated based on the face image as shown in FIG. 2, and in response to the state of the cervical spine possibly falls outside a normal range, the state of the user's cervical spine may be finally determined based on the degree of inclination of the portable terminal as shown in FIG. 3. In addition, even in response to the state of the cervical spine falling outside a normal range, whether the user using the portable terminal is in an incorrect posture may be determined based on a result of an estimation of whether the state outside the normal range is maintained longer than a reference period of time.

Figure 4:
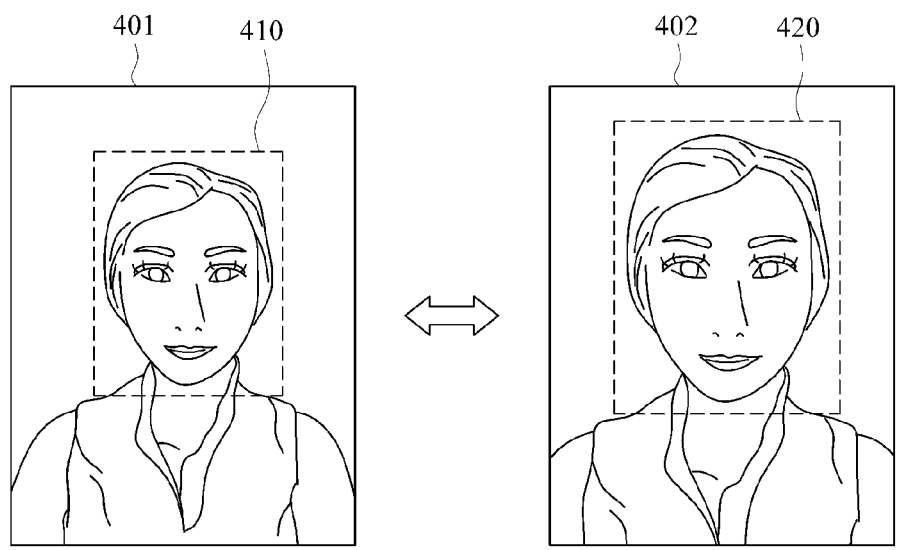
FIG. 4 is a diagram illustrating an example of a method of estimating a state of viewing a portable terminal.

FIG. 4 illustrates an example of a method of estimating a state of viewing a portable terminal.

Referring to FIGS. 1 and 4, the determining unit 101 may compare a previously stored reference face image 401 and a currently captured face image 402, and based on the comparison, the determining unit 101 may estimate a state of the user's viewing a portable terminal that corresponds to a distance between the user's eyes and the portable terminal.

The reference face image 401 may be an image of the user in a correct posture. The determining unit 101 may compare a ratio of the area of a face region 410 to the entire reference face image 401 and a ratio of the area of a face region 420 to the currently captured face image 402 to determine whether the state of viewing the portable terminal is in a normal range or falls outside a normal range. In the case of a plurality of reference face images 401, the ratio of the area of a face region 410 to the reference face image may be obtained from the average of ratios of the areas of the face region to each of the reference face images 401. As a distance between the user's eyes and the portable terminal becomes closer, the ratio of the area of each of the face regions 410 and 420 to the respective entire face image 401 and 402 increases. Accordingly, in response to the ratio of the area of each of the face regions 410 and 420 to the respective face images 401 and 402 falls outside a predefined threshold range, for example, the user may be watching the portable terminal too close, and thus the determining unit 101 may determine that the state of the viewing the portable terminal falls outside a normal range. In addition, since the state of the viewing the portable terminal may fall outside a normal range, the determining unit 101 may determine that the user is using the portable terminal in an improper posture.

Figure 5:
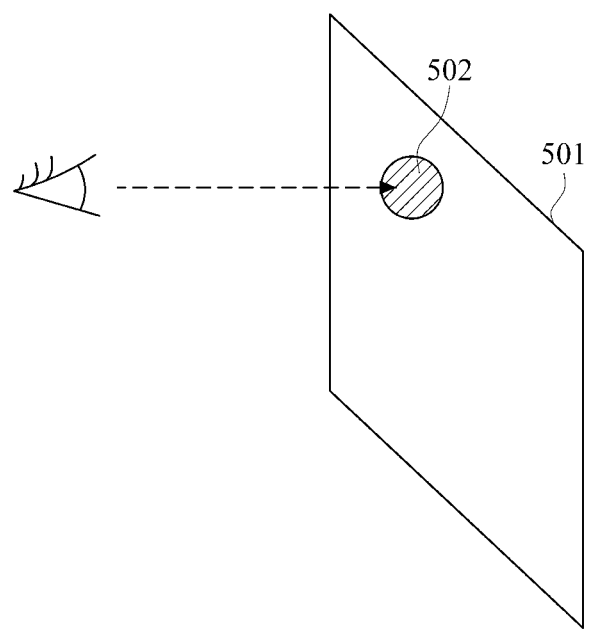
FIG. 5 is a diagram illustrating another example of a method of estimating a state of a user's viewing a portable terminal.

FIG. 5 illustrates another example of a method of estimating a state of a user's viewing a portable terminal.

Referring to FIGS. 1 and 5, the determining unit 101 may determine whether the state of the viewing the portable terminal is in a normal range or falls outside a normal range based on the user's eye movement in a captured face image. The determining unit 101 may identify where the user's eyes are looking or number of eye-blinks through the eye-tracking technology. For example, in response to the user looking at a specific part 502 of a screen of the portable terminal, the determining unit 101 may measure a time the user is continuously looking at the point 502 (i.e., viewing time) and the number of eye-blinks that occurred while continuously looking at the point 502. In response to the user looking at the point 502 for longer than a predefined period of time or in response to the number of eye-blinks being less than a predefined number, the determining unit 101 may determine that the state of the user's viewing the portable terminal falls outside a normal range. Moreover, in response to the state of the user's viewing the portable terminal falling outside the normal range, the determining unit 101 may determine that the user using the portable terminal is in an improper posture.

The examples illustrated in FIGS. 4 and 5 describe a method of estimating a state of a user's viewing the portable terminal based on a distance between the user's eyes and the portable terminal and based on the information about the user's eye movement. As another aspect, these examples are for illustrative purposes, and the method of estimating the state of the user's viewing the portable terminal is not limited thereto. For example, as shown in FIG. 4, the state of the viewing the portable terminal may be preliminarily determined based on a distance between the user's eyes and the portable terminal, and only in response to the determination showing that the state of the user's viewing may fall outside a normal range, the final determination on the state of the user's viewing may be made based on the information about the user's eye movement as shown in FIG. 5. Also, although the state of the user's viewing the portable terminal may fall outside a normal range, a determination on whether the user is using the portable terminal in a correct posture or in an incorrect posture further based on the determination of whether the state outside the normal range of viewing occurs for a time longer than a predefined reference period of time.

Figure 6:
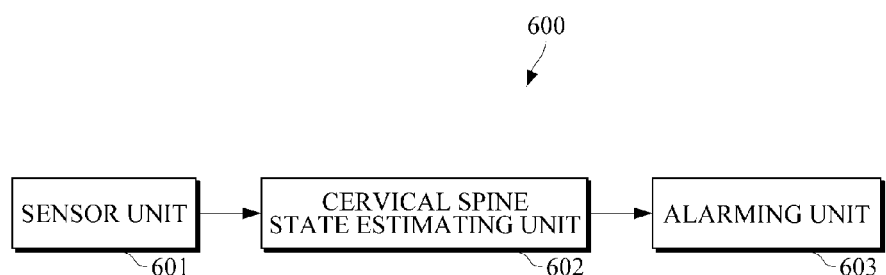
FIG. 6 is a diagram illustrating another example of an apparatus for assisting a user to maintain a correct posture during use of a potable terminal.

FIG. 6 illustrates another example of an apparatus for assisting a user to maintain a correct posture during use of a portable terminal.

Referring to FIG. 6, apparatus 600 may include a sensor unit 601, a cervical spine state estimating unit 602, and an alarming unit 603.

The sensor unit 601 may collect information about a face image of a user and information about an angle of inclination of a portable terminal. The sensor unit 601 may include a front camera and a variety of sensors, which are equipped in the portable terminal. The variety of sensors may include an orientation sensor, an acceleration sensor, a magnetic sensor, and the like. The front camera may be installed on a front of the portable terminal to capture an image of a user's face. The orientation sensor may be installed inside of the portable terminal to measure an azimuth, a pitch, and a roll of the portable terminal. The acceleration sensor and the magnetic sensor may be installed inside of the portable terminal to measure the acceleration or the magnitude of a magnetic field of the portable terminal in motion. The acceleration or the magnitude of a magnetic field may be measured with respect to a direction of a 3-dimensional axis. The front camera may obtain the face image of the user. A pitch value of the orientation sensor may be used as the inclination angle of the portable terminal. In addition, a result of application of the measured values of the acceleration sensor and the magnetic sensor to a rotation matrix may be used as the inclination angle of the portable terminal.

The cervical spine state estimating unit 602 may estimate a state of the user's cervical spine. For example, the cervical spine state estimating unit 602 may determine whether the state of the user's cervical spine is in a normal range or falls outside the normal range.

Information used in estimating the state of the cervical spine may be the face image of the user, the inclination angle of the portable terminal, or any combination thereof.

An example of use of only a face image is described. As shown in the example illustrated in FIG. 2, the cervical spine state estimating unit 602 may compare the reference face image 201 and the currently received face image 202 to determine whether the user is lowering his or her head. For example, a shape of the face, a ratio of the area of the face to the area of the neck, and the brightness of the face may be used as features to be compared. In response to the user lowering his or her cervical spine for longer than a predefined reference period of time, a determination may be made that the cervical spine of the user falls outside a normal state.

An example of use of only an inclination angle of the portable terminal is described. As shown in the example illustrated in FIG. 3, the cervical state estimating unit 602 takes into consideration that the inclination angle 310 of the portable terminal is substantially the same as the tilt angle 320 of the user's head, and then determines whether the inclination angle 310 of the portable terminal is lower than a predefined threshold angle. In response to the inclination angle 310 of the portable terminal being lower than the predefined threshold angle and the inclination angle 310 being maintained for longer than a predefined reference period of time, the cervical state estimating unit 602 may determine that the user's cervical spine falls outside a normal state.

As another example, both the face image and the inclination angle of the portable terminal may be used to estimate the state of the user's cervical spine. For example, the approximate state of the user's cervical spine may be estimated based on the face image of the user, and then the detailed state of the user's cervical spine may be estimated based on the inclination angle of the portable terminal. In other words, the current posture may be approximately estimated and the current posture may be determined whether the current posture may harm the user's cervical spine based on the face image. In response to the current posture being harmful, a final determination may be made whether the state of the user's cervical spine is in a normal range or falls outside a normal range. The final determination may be based on a result of comparison between a current inclination angle of the portable terminal and an average of various reference inclination angles of the portable terminal held by the user in a correct posture.

In response to the cervical spine state estimating unit 602 determining that the user's cervical spine falls outside a normal state, the alarming unit 603 may provide an alarm. The alarm is not limited by its type. For example, the alarming unit 603 may provide an alarm in the form of an image, text, sound, vibration, or any form of alarm that can notify the user to change the posture.

Figure 7:
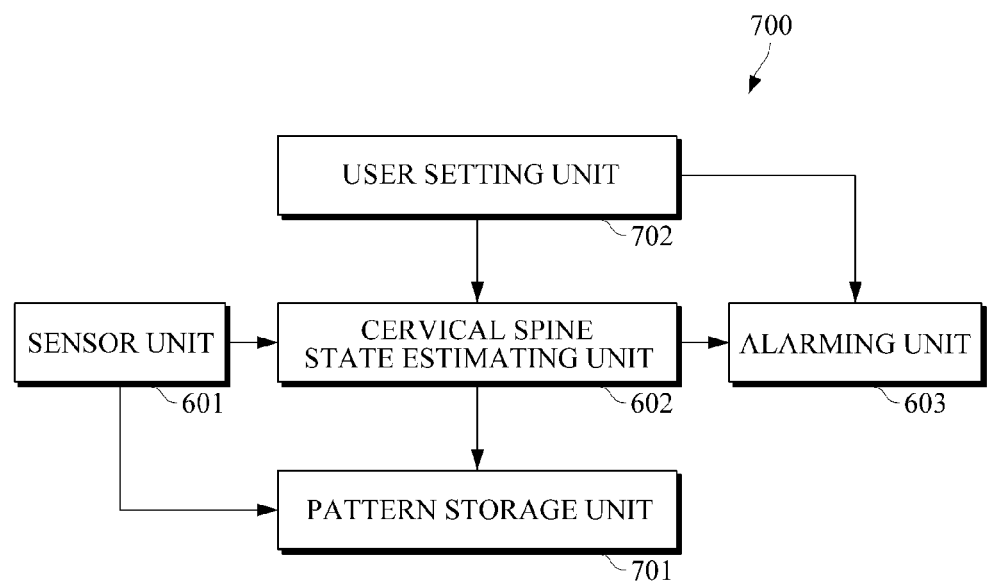
FIG. 7 is a diagram illustrating another example of an apparatus for assisting a user to maintain a correct posture during use of a portable terminal.

FIG. 7 illustrates another example of an apparatus for assisting a user to maintain a correct posture during use of a portable terminal.

Referring to FIG. 7, apparatus 700 includes a sensor unit 601, a cervical spine state estimating unit 602, an alarming unit 603, a pattern storage unit 701, and a user setting unit 702. The sensor unit 601, the cervical spine state estimating unit 602, and the alarming unit 603 may be substantially similar as those shown in the example illustrated in FIG. 6. Thus, a description of the sensor unit 601, the cervical spine state estimating unit 602, and the alarming unit 603 will not be reiterated for conciseness.

The pattern storage unit 701 may store an estimated state of the cervical spine, a tilt angle of the cervical spine at the time of estimation, and feature information of a face image at the time of estimation. The pattern storage unit 701 may receive a face image of the user and the inclination angle of the portable terminal from the sensor unit 601. The pattern storage unit 701 may extract features from the received face image, and the pattern storage unit 701 may store the extracted features and the inclination angle of the portable terminal in a database. An example of the database may be shown in Table 1 below.

TABLE 1

| Face Shape | Ratio of Area of Face to Entire Face Image | Ratio of Area of Neck to Entire Face Image | Face Brightness (1~10) | Inclination Angle of Portable Terminal (pitch) |
|---|---|---|---|---|
| Oval | 23% | 5% | 8 | −91 |

Because features of the face image at various states of the cervical spine differ according to the individual user and the image capturing condition, capturing a reference face image of the user may generate learning data. For example, a correct posture image or a poor posture image may establish learning data. The pattern storage unit 701 may establish the database (including the learning data). The database may be utilized by the cervical spine state estimating unit 602 to classify face images.

In response to a user's input, the user setting unit 702 may set a parameter of the cervical spine state estimating unit 602, a type of alarming to be provided by the alarming unit 603, or any combination thereof. The parameter of the cervical spine state estimating unit 602 may include various threshold values and a reference time for determining the normal or a state outside the normal range of the cervical spine, or a type of features for use in image classification.

Figure 8:
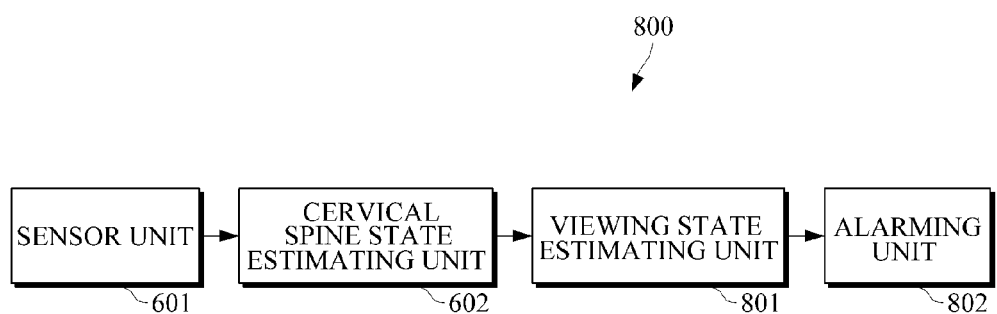
FIG. 8 is a diagram illustrating another example of an apparatus for assisting a user to maintain a correct posture during use of a portable terminal.

FIG. 8 illustrates another example of an apparatus for assisting a user to maintain a correct posture during use of a portable terminal.

Referring to FIG. 8, apparatus 800 includes a sensor unit 601, a cervical spine state estimating unit 602, a viewing state estimating unit 801, and an alarming unit 802. The sensor unit 601 and the cervical spine state estimating unit 602 are substantially similar as those in the example illustrated in FIG. 6. Thus, a description of the sensor unit 601 and the cervical spine state estimating unit 602 will not be reiterated for conciseness.

The viewing state estimating unit 801 may estimate the state in which the user is viewing a portable terminal. The state of viewing the portable terminal may indicate whether a distance between the user's eyes and the portable terminal, a degree of user's concentration on the portable terminal is within a normal range or not, or any combination thereof.

An example of using a distance between the user's eyes and the portable terminal to determine the state of viewing the portable terminal is described. For example, the viewing state estimating unit 801 may estimate the distance between the user's eyes and the portable terminal based on the ratio of the area of the face region 420 to a captured face image 402 as shown in FIG. 4. In response to the distance being closer than a threshold distance and the current distance being main-tained for longer than a reference period of time, the viewing state estimating unit 801 may determine that the state of viewing the portable terminal falls outside a normal range.

An example of using a degree of concentration on the portable terminal to determine the state of viewing the portable terminal is described. For example, the viewing state estimating unit 801 may estimate the degree of concentration on the portable terminal on the basis of information about the eye movement. For example, the information about the eye movement may be a period of viewing the portable terminal or the number/time of eye-blinks. In response to the degree of concentration on the portable terminal going over a threshold range and the current state being maintained for longer than a reference period of time, the viewing state estimating unit 801 may determine that the state of the user's viewing the portable terminal falls outside a normal state.

In addition, both the distance between the user's eyes and the portable terminal and the degree of concentration on the portable terminal may be identified. In response to either the distance or the degree of the concentration going beyond the threshold range, the state of the viewing the portable terminal falls outside a normal range. As another example, the state of viewing the portable terminal may be preliminarily determined based on the distance between the user's eyes and the portable terminal, and then the final determination on the viewing state may be made based on the degree of concentration on the portable terminal.

In response to the cervical state estimating unit determining that the state of the user's cervical spine falls outside a normal range, or in response to the viewing state estimating unit 801 determining that the state of viewing the portable terminal falls outside a normal range, the alarming unit 802 may provide a predetermined type of alarm. The type of the alarm may vary.

Figure 9:
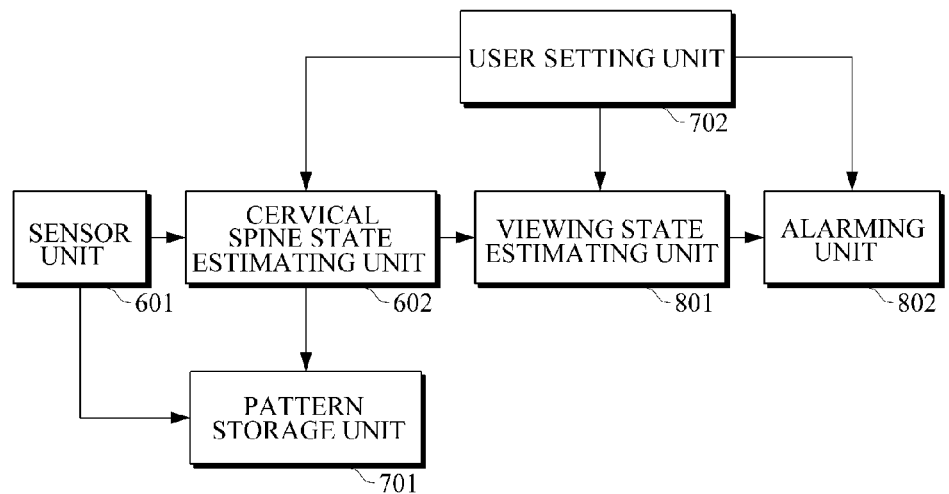
FIG. 9 is a diagram illustrating another example of an apparatus for assisting a user to maintain a correct posture during use of a portable terminal.

FIG. 9 illustrates another example of an apparatus for assisting a user to maintain a correct posture during use of a portable terminal.

Referring to FIG. 9, apparatus 900 includes a sensor unit 601, a cervical spine state estimating unit 602, a viewing state estimating unit 801, an alarming unit 802, a pattern storage unit 701, and a user setting unit 702. The configuration and operation of each unit of the apparatus 900 shown in the example illustrated in FIG. 9 are substantially similar to those in the apparatuses shown in the examples illustrated in FIGS. 6 to 8, and thus they are represented by the same numerals and detailed description thereof will not be reiterated for conciseness.

However, unlike the apparatus illustrated in FIG. 7, the user setting unit 702 of the apparatus illustrated in FIG. 9 may additionally set the parameter for the viewing state estimating unit 801.

Figure 10:
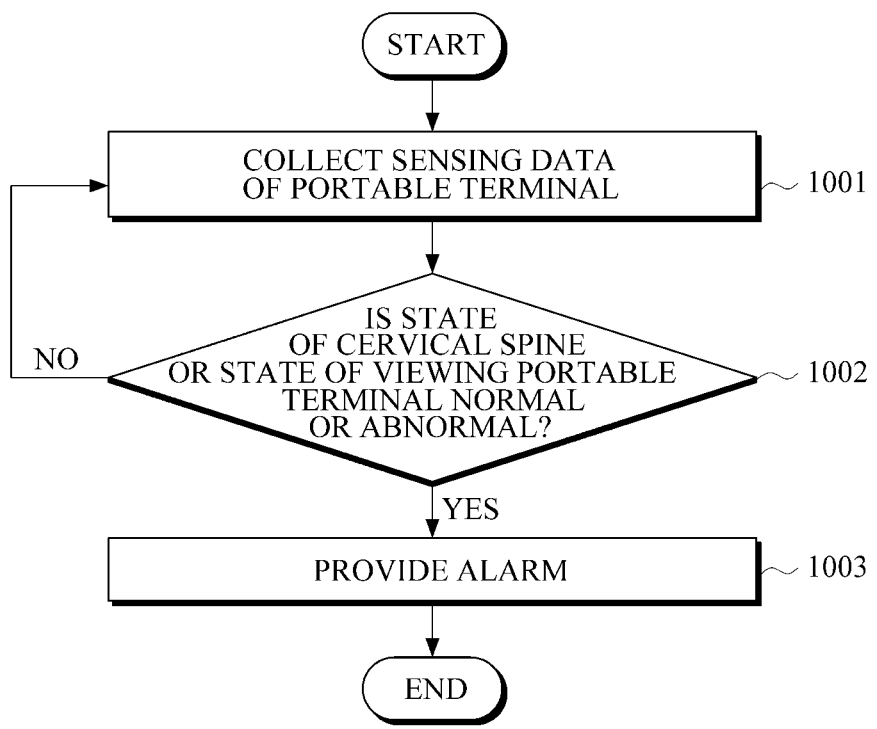
FIG. 10 is a flowchart illustrating an example of a method for assisting a user to maintain a correct posture during use of a portable terminal.

FIG. 10 illustrates an example of a method for assisting a user to maintain a correct posture during use of a portable terminal.

Referring to FIG. 10, sensing data of a portable terminal may be collected at 1001. The sensing data to be collected may be data obtained by native S/W or H/W capabilities of the apparatus without requiring additional sensors. For example, the sensing data may include a front image and positional information of the portable terminal during use of the portable terminal. In other words, the front image may be a face image of a user. The positional information may be sensing data obtained by an orientation sensor, an acceleration sensor, a magnetic sensor, and the like.

In response to the sensing data being collected, the method may determine whether the state of the user's cervical spine or the state of user's viewing the portable terminal falls outside a normal range at 1002. The state of the cervical spine may indicate an angle of the user's head with respect to the user's body. The angle may correspond with a tilt angle of the cervical spine, and the method may determine whether the angle falls within a normal range or outside a normal range. The state of viewing the portable terminal may indicate whether the degree of strain on the user's eyes or the user's posture falls within a normal range or outside a normal range during use of the portable terminal. The state of the cervical spine may be estimated based on the face image as illustrated in FIG. 2, the inclination angle of the portable terminal as illustrated in FIG. 3, or any combination thereof. The state of viewing the portable terminal may be estimated based on the distance between the user's eyes and the portable terminal as illustrated in FIG. 4, the degree of concentration on the portable terminal as illustrated in FIG. 5, or any combination thereof.

In a case in which the state of the cervical spine or the state of viewing the portable terminal falls outside a normal state, a predetermined type of alarm may be provided at 1003. The type of alarm may vary. For example, the alarm may be an image, text, sound, vibration, or any form of alarm that can notify the user to change the posture.

As described above, a determination whether a user is using a portable terminal in a correct posture based on sensing data obtained by sensors natively equipped in the portable terminal without additional sensors may be possible, and in response to a determination being made that the user is not in a correct posture, providing an alarm to promote the user to change his or her pose may be possible. Accordingly, any trouble or disorder due to a poor posture during use of the portable terminal may be prevented from occurring.

Program instructions to perform a method described herein, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of computer-readable media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable recording mediums. Also, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein. Also, the described unit to perform an operation or a method may be hardware, software, or some combination of hardware and software. For example, the unit may be a software package running on a computer or the computer on which that software is running.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for assisting a user to maintain a correct posture, the apparatus being a portable terminal and comprising:
  a processor configured to estimate a state of a user's cervical spine based on an angle of inclination sensed by a sensor of the portable terminal, the sensor being in communication with the processor so that the processor is configured to determine a result of whether the user is using the portable terminal in a correct posture based on the state of the user's cervical spine not being in a predefined range for a predefined amount of time based on a result of a comparison between a predefined threshold value and the angle of inclination sensed by the sensor of the portable terminal; and
  an alarming unit in communication with the processor and configured to generate a predetermined alarm according to the determination result determined by the processor.

2. The apparatus of claim 1, wherein the processor is configured to estimate a degree of tilt of the user's cervical spine as the state of the cervical spine.

3. The apparatus of claim 1, further comprising:
  a sensor unit comprising the imaging device configured to capture a face image of the user and the sensor configured to sense the angle of inclination of the portable terminal.

4. The apparatus of claim 1, wherein the processor is further configured to determine whether the state of the user's cervical spine is in the predefined range or falls outside the predefined range based on a result of a comparison between a previously stored reference face image of the user and a current face image of the user captured by an imaging device of the portable terminal, the imagining device being in communication with the processor so as to permit the determination of whether the state of the user's cervical spine is in the predefined range.

5. The apparatus of claim 1, further comprising:
  a user setting unit configured to set a parameter for the processor and a type of the alarm to be provided by the alarming unit in response to a user's input.

6. The apparatus of claim 1, wherein the state of the cervical spine is the angle of the user's head with respect to the user's torso.

7. The apparatus of claim 1, wherein the predetermined alarm includes an alarm message on a display of the portable terminal, an alarming sound, a vibration, or a decrease in power sent to the display.

8. An apparatus for assisting a user to maintain a correct posture, the apparatus being a portable terminal and comprising:
  a processor configured to estimate a state of a user's cervical spine based on at least one of a user's face image captured by an imaging device of a portable terminal and an angle of inclination sensed by a sensor of the portable terminal, each of the imaging device and the sensor being in communication with the processor so that the processor is configured to determine a result of whether the user is using the portable terminal in a correct posture based on the state of the user's cervical spine not being in a predefined range for a predefined amount of time, wherein the result is based preliminarily on a result of a comparison between a previously stored reference face image and a current face image captured by the imaging device of the portable terminal and finally on a result of a comparison between a predefined threshold value and the angle of inclination of the portable terminal sensed by the sensing device of the portable terminal; and an alarming unit in communication with the processor and configured to generate a predetermined alarm according to the determination result determined by the processor.

9. An apparatus for assisting a user to maintain a correct posture, the apparatus being a portable terminal and comprising:

a processor configured to estimate a state of a user's cervical spine based on at least one of a user's face image captured by an imaging device of a portable terminal and an angle of inclination sensed by a sensor of the portable terminal, each of the imaging device and the sensor being in communication with the processor so that the processor is configured to determine a result of whether the user is using the portable terminal in a correct posture based on the state of the user's cervical spine not being in a predefined range for a predefined amount of time;

an alarming unit in communication with the processor and configured to generate a predetermined alarm according to the determination result determined by the processor;

a sensor unit comprising the imaging device configured to capture the user's face image and the sensor configured to sense the angle of inclination of the portable terminal; and a storage device configured to receive the user's face image and the angle of inclination of the portable terminal from the sensor unit, to extract features from the face image, and to store a result of matching between the extracted features and the angle of inclination of the portable terminal.

10. A method for assisting a user to maintain a correct posture when using a portable terminal, the method comprising:

estimating a state of a user's cervical spine based on at least one of a user's face image captured by an imaging device of a portable terminal and an angle of inclination sensed by a sensing device of the portable terminal;

determining, based on communication between each of the imaging device and the sensing device with the portable terminal, whether the user is using the portable terminal in a correct posture based on the state of the user's cervical spine not being in a predefined range for a predefined amount of time, wherein the determining comprises determining whether the state of the user's cervical spine is in a predefined range or falls outside the predefined range based on a result of a comparison between a predefined threshold value and the angle of inclination of the portable terminal; and generating a predetermined alarm in response to the state of the user's cervical spine falling outside the predefined range.

11. The method of claim 10, wherein the determining further comprises determining whether the state of the user's cervical spine is in a predefined range or falls outside the predefined range based on a result of comparison between a previously stored reference face image and a current face image captured by the imaging device of the portable terminal.

12. A method for assisting a user to maintain a correct posture when using a portable terminal, the method comprising:

estimating a state of a user's cervical spine based on at least one of a user's face image captured by an imaging device of a portable terminal and an angle of inclination sensed by a sensing device of the portable terminal;

determining, based on communication between each of the imaging device and the sensing device with the portable terminal, whether the user is using the portable terminal in a correct posture based on the state of the user's cervical spine not being in a predefined range for a predefined amount of time, wherein the determining comprises preliminarily determining whether the state of the user's cervical spine is in a predetermined range or falls outside the predefined range based on a result of a comparison between a previously stored reference face image and a current face image captured by the imaging device of the portable terminal and finally determining whether the state of the user's cervical spine is in the predefined range or falls outside the predefined range based on a result of a comparison between a predefined threshold value and the angle of inclination of the portable terminal sensed by the sensing device of the portable terminal, and generating a predetermined alarm in response to the state of the user's cervical spine falling outside the predefined range.

* * * * *